United States Patent [19]

Perazzo et al.

[11] Patent Number: 5,043,205
[45] Date of Patent: Aug. 27, 1991

[54] NOISELESS POLYMERIC FILM, AND CONTAINERS FOR MEDICAL USE MADE THEREOF

[75] Inventors: Luigi Perazzo, Cuneo; Francesco Martini, Rho, both of Italy

[73] Assignee: W. R. Grace & Co.-Conn., Duncan, S.C.

[21] Appl. No.: 382,377

[22] Filed: Jul. 20, 1989

Related U.S. Application Data

[62] Division of Ser. No. 203,386, Jun. 7, 1988, abandoned.

[30] Foreign Application Priority Data

Nov. 26, 1987 [IT] Italy ............................. 22771 A/87

[51] Int. Cl.⁵ ..................... B32B 27/08; C08L 63/00; C08L 23/28; A61F 13/16
[52] U.S. Cl. ..................... 428/215; 428/518; 428/520; 525/227; 604/372
[58] Field of Search ................ 428/215, 518, 520

[56] References Cited

U.S. PATENT DOCUMENTS

| | | | |
|---|---|---|---|
| 3,950,281 | 4/1976 | Usamoto et al. | 260/4 |
| 4,376,799 | 3/1983 | Tusim | 428/213 |
| 4,798,602 | 1/1989 | Laus | 604/372 |
| 4,822,838 | 4/1989 | Watanabe | 524/178 |

FOREIGN PATENT DOCUMENTS 2131816 6/1984 United Kingdom .
2138431 10/1984 United Kingdom .

*Primary Examiner*—P. C. Sluby
*Attorney, Agent, or Firm*—John J. Toney; William D. Lee, Jr.; Mark B. Quatt

[57] ABSTRACT

The film is formed by a composition comprising a mixture of 50-100 weight % of an ethylene-butyl-acrylate copolymer (EBA) having a content of butyl-acrylate (BA) of 5-50 weight %, and 0-50 weight % of an elastomeric polyolefin. Laminates comprising a layer constituted by said film have excellent characteristics of noiselessness and softness.

13 Claims, No Drawings

NOISELESS POLYMERIC FILM, AND CONTAINERS FOR MEDICAL USE MADE THEREOF

This is a divisional application of application Ser. No. 203,386, filed on June 7, 1988 now abandoned.

DESCRIPTION

The present invention relates to a polymeric film with improved properties of noiselessness or silence as well as of softness and flexibility, and relates to containers and bags for medical use which are made of said film.

For certain applications, in particular of the medical type, containers are required which are used in contact with the skin, such as, for example, containers or bags for surgical drainage called "ostomy" pouches, destined to collect secretions or excretory products of patients who have undergone surgical interventions. The use of such containers may be temporary or for the remainder of a patient's life.

The principle requisite which such containers must satisfy is that of being unnoticable to the greatest extent possible, both by the patient himself and by other people. To this end, they should be soft and almost imperceptible upon contact with the skin, they must not rustle or produce noise in use, and furthermore, they must have good properties of durability, abrasion and puncture resistance, and be a barrier to odors and gasses in general.

Various solutions to this problem have been proposed to date, among which is patent application GB 8309722 which proposes the use of a film basically composed of polymeric mixtures of polyolefin, chlorinated polyolefin, and chlorinated paraffin.

The patent EP 59739 describes a composite shock-resistant film based on a polymeric mixture of at least 40% of chlorinated polyolefin with a polyolefin.

Italian patent 1.163.372 describes the use of a film based on a mixture of ethylene-vinylacetate copolymer (EVA) with elastomeric polyolefin which also comprises a certain proportion of EVA.

The main object of the present invention is to provide a film having superior characteristics of noiselessness and flexibility combined with exceptional characteristics of softness and comfort in contact with the skin.

An object of the present invention is to provide a composite film, and containers for medical use made of said film, which are noiseless, flexible and soft.

A not least object of the present invention is to provide containers as mentioned above, which have good characteristics of being a barrier to odors, and of mechanical resistance.

These and other objects which will become apparent hereinafter are acheived by a film according to the invention, having improved characteristics of noiselessness, softness, and flexibility, formed by a composition comprising from 50 to 100 weight % of an ethylene-butyl-acrylate copolymer having a content of butyl-acrylate of 5-50 weight %, mixed with 0-50 weight % of at least one elastomeric polymer.

According to another aspect of the invention, the proposed objects are achieved by a multilayer laminated film comprising at least one layer formed by a noiseless, flexible and soft film according to the invention, and at least one other layer adapted to function as a barrier to gas and odors.

The present invention is based on the use of an ethylene-butyl-acrylate copolymer (EBA) to form at least one layer of a multilayer laminated film to impart to the laminated film, exceptional characteristics of noiselessness and softness upon contact with the skin, in addition to the characteristic of mechanical resistance, in particular durability, abrasion and puncture resistance, as well as being heat-sealable.

The EBA copolymer can have a content of butyl-acrylate (BA) of 5-50 weight %, preferably 7 to 30 weight %, and a molecular weight corresponding to a Melt Flow Index (MFI) from 1 to 7 g/10 min.

EBA copolymers of this type are available, for example, from the NESTE OY company in Finland, and are sold under the name NESTE DFDS 6440, 6427, and 6470.

EBA copolymer can be used alone or in a mixture with up to 50 weight % of the mixture being constituted by an elastomeric polymer, in particular an elastomeric polyolefin. The elastomeric polyolefin may be chosen, for example, from, ethylene-propylene rubbers having an ethylene content of at least 50%, ethylene-propylene-diene rubbers having an ethylene content of at least 50% or chlorinated polyethylene having a chlorine content of at least 20%.

The composition of the film or layer of EBA of a multilayer laminated film according to the invention may further comprise from 0.1 to 5 weight % of an additive such as an anti-blocking agent, a flowing agent, a plasticizer, a stabilizer, an extrusion coadjutant, or a mixture thereof. Such additives may be selected from those which are conventionally used for the desired purpose. For example, as an anti-blocking agent, one may use a silica gel such as that sold by W. R. Grace (U.S.A.) under the name Syloblock; as a flowing agent one may use amidic waxes such as erucamide or ethylene-bis-stearamide, and as a plasticizer one may use epoxydized soyabean oil or chlorinated paraffin, such as, for example, that sold by the Hoechst company under the name CERECLOR 56.

The multilayer laminated film according to the invention comprises at least one of the above-mentioned layers of EBA together with other layers formed in polymeric material suitable for the envisaged use.

In particular, for use in drainage containers for medical use, the laminated film comprises at least one layer having the function of providing a barrier against odors and gasses. Any type of polymeric material may be used to carry out the barrier function, and preferably a polymer selected from vinylidene chloride polymers and (PVDC) copolymers with comonomers selected from acrylic esters, acrylic acid, and vinyl chloride, ethylenevinylalcohol (EVOH) copolymers, vinylidene fluoride-vinyl fluoride copolymers, polyamides and mixtures thereof.

Preferably, the laminated film acording to the invention comprises at least three layers of which an internal layer functions as a barrier interposed between two external layers. For the external layers, either two layers of EBA may be used as described above, or one layer of EBA and one further layer of another polymer selected from olefin copolymers with a comonomer selected from vinyl acetate and acrylate esters.

The thickness of the laminated film according to the invention may vary from 30 to 150/$\mu$, with the layer or layers of EBA constituting at least 50% of the total thickness. Usually, the barrier layer has a thickness which varies from 5 to 25/μ, whilst each of the external layers has a thickness between 5 and 70/μ.

The laminated film may include further layers, for example, intermediate binding layers which improve the adhesion between the external EBA layers and the barrier layer, or layers which improve certain properties of the laminated film such as the mechanical resistance, heat sealability, etc. To this end, known polymers or copolymers may be used for imparting the abovementioned properties, according to neccessity.

The laminated film according to the invention can be obtained by means of conventional technology, for example, by coextrusion of the EBA copolymer adjacent to a barrier layer on one or both of its sides, with or without the interposition of binding layers, or alternatively by the coextrusion of other polymers or copolymers to form other required layers. Before extrusion, the ingredients of the composition destined to form the layer or layers of EBA can be mixed and granulated by means of a double screw extruder. The coextrusion of the different layers of the laminate can be carried out by means of the technique of coextrusion through a circular die with multiple concentric slots by using the insufflation of a bubble of hot air, whereupon the coextrusion is cooled, cut into segments of desired length and welded, for example by high frequency or heat to produce containers or bags for medical use.

The following exclusively illustrative, non-limitative examples show some possible embodiments of the laminated film according to the present invention.

EXAMPLE 1

Various laminated films with three layers A/B/C were prepared which had the following composition:
Layer A: 100% EBA [NESTE DFDS 6440 (17% BA, MFI 2)], 40 microns.
  or: 50% EBA [NESTE DFDS 6427 (27% BA, MFI 4)]+50% ethylene-propylene rubber [DUTRAL CO 034 PLF], thickness 40 microns.
  or: 50% EBA [NESTE DFDS 6470 (7% BA, MFI 1)]+50% ethylene-propylene-diene rubber [DSM KELTAN TP 9200], thickness 40 microns.
  or: 60% EBA [NESTE 6440]+35% chlorinated polyethylene [HOECHST HOSTAPREN 803 (36% Cl)]+5% plasticizer [HOECHST CERECLOR 56 (56% Cl)], thickness 45 microns.
Layer B: is PVDC, thickness 15 microns.
  or: is EVOH, thickness 10 microns.
Layer C: is the same as layer A
  or: ethylene-vinyl acetate copolymer [DUPONT ELVAX 3165 (18% VA, MFI 0.8)], thickness 20 microns.
  or: ethylene-methylacrylate copolymer [GULF 2255 (18% MA, MFI 2)], thickness 20 microns.

EXAMPLE 2

Various laminated films with five layers D/E/F/G/H were prepared which had the following composition:
Layer D: is the same as layer A of example 1
Layer E: is 100% EBA [NESTE DFDS 6427 (27% BA, MFI 4)], thickness 10 microns.
  or: ethylene-vinyl acetate copolymer [DU PONT ELVAX 3175 (28% VA, MFI 7)] thickness 5 microns.
  or: a modified EVA [DU PONT BYNEL CXA-E-162], thickness 5 microns.
Layer F: is the same as layer B of example 1
Layer G: is the same as layer E
Layer H: is the same as layer C of example 1.

What is claimed is:

1. A multilayer film having characteristics of noiselessness, softness, and flexibility comprising:
  a) two outer layers comprising an olefinic polymer or copolymer;
  b) an intermediate layer comprising a polymeric material which functions as a gas barrier; and
  c) at least one of the outer layers consisting essentially of ethylene butyl acrylate copolymer having 5 to 50 weight % butyl acrylate, or a blend with up to 35% by weight of at least one elastomeric polyolefin.

2. The multilayer film of claim 1 wherein the polymeric material which functions as a gas barrier is selected from the group consisting of:
  a) vinylidene chloride polymer;
  b) vinylidene chloride copolymer with comonomer selected from the group consisting of acrylic esters, acrylic acid, and vinyl chloride;
  c) ethylene vinyl alcohol copolymer;
  d) polyamides; and
  e) mixtures of these materials.

3. The multilayer film of claim 1 wherein the elastomeric polyolefin of at least one of the outer layers is a polymeric material selected from the group consisting of elastomeric polyolefin, ethylene propylene rubber, ethylene propylene diene rubber, and chlorinated polyethylene.

4. The multilayer film of claim 1 wherein at least one of the outer layers further comprises between about 0.1% and 5% by weight of at least one additive selected from the group consisting of antiblocking agents, flowing agents, plasticizers, stabilizers, and extrusion coadjutants.

5. The multilayer film of claim 1 wherein the film has a total thickness of between about 20 and 150 microns, and the layers containing the ethylene butyl acrylate copolymer constitute at least about 50% of the total film thickness.

6. The multilayer film of claim 1 wherein the film is coextruded.

7. A multilayer film having characteristics of noiselessness, softness, and flexibility comprising:
  a) two outer layers comprising an olefinic polymer or copolymer;
  b) an intermediate layer comprising a polymeric material which functions as a gas barrier;
  c) a binding polymeric layer disposed between and bonding the intermediate layer to each respective outer layer; and
  d) at least one of the outer layers consisting essentially of ethylene butyl acrylate copolymer having 5 to 50 weight % butyl acrylate, or a blend with up to 35% by weight of at least one elastomeric polyolefin.

8. The multilayer film of claim 7 wherein the polymeric material which functions as a gas barrier is selected from the group consisting of:
  a) vinylidene chloride polymer;
  b) vinylidene chloride copolymer with comonomer selected from the group consisting of acrylic esters, acrylic acid, and vinyl chloride;
  c) ethylene vinyl alcohol copolymer;
  d) polyamides; and
  e) mixtures of these materials.

9. The multilayer film of claim 7 wherein the binding layer is a polymeric material selected from the group consisting of ethylene butyl acrylate copolymer, ethylene vinyl acetate copolymer, and modified ethylene vinyl acetate copolymer.

10. The multilayer film of claim 7 wherein the elastomeric polyolefin of at least one of the outer layers is a polymeric material selected from the group consisting of elastomeric polyolefin, ethylene propylene rubber, ethylene propylene diene rubber, and chlorinated polyethylene.

11. The multilayer film of claim 7 wherein at least one of the outer layers further comprises between about 0.1% and 5% by weight of at least one additive selected from the group consisting of antiblocking agents, flowing agents, plasticizers, stabilizers, and extrusion coadjutants.

12. The multilayer film of claim 7 wherein the film has a total thickness of between about 20 and 150 microns, and the layers containing the ethylene butyl acrylate copolymer constitute at least about 50% of the total film thickness.

13. The multilayer film of claim 7 wherein the film is coextruded.

* * * * *